United States Patent [19]

Pettman et al.

[11] Patent Number: 4,782,053

[45] Date of Patent: Nov. 1, 1988

[54] FUNGICIDAL COMPOSITIONS

[75] Inventors: Roger B. Pettman, Wychling; Paul J. Kuhn, Faversham, both of England

[73] Assignee: Shell Internationale Research Maatschappij B.V., The Hague, Netherlands

[21] Appl. No.: 90,275

[22] Filed: Aug. 28, 1987

[30] Foreign Application Priority Data

Sep. 23, 1986 [GB] United Kingdom ............... 8622900

[51] Int. Cl.$^4$ ............... A01N 43/56; A01N 43/64; A01N 43/84
[52] U.S. Cl. ............... 514/231.2; 514/383; 514/397; 514/400; 514/239.5
[58] Field of Search ............... 514/227, 232, 236, 237, 514/238, 240, 326, 341, 383, 397, 400

[56] References Cited

U.S. PATENT DOCUMENTS

| | | | |
|---|---|---|---|
| 2,897,113 | 7/1959 | Gruenhagen et al. | 514/227 |
| 3,686,399 | 8/1972 | Sanne et al. | 514/227 |
| 4,434,165 | 2/1984 | Bohnen | 514/227 |
| 4,472,412 | 9/1984 | Buschmann et al. | 514/227 |
| 4,596,801 | 6/1986 | Sugiyama et al. | 514/227 |

FOREIGN PATENT DOCUMENTS

| | | |
|---|---|---|
| 1201716 | 3/1986 | Canada. |
| 0072156 | 2/1983 | European Pat. Off. ............ 514/227 |
| 0191514 | 8/1986 | European Pat. Off. |
| 253447 | 1/1988 | European Pat. Off. . |
| 2633874 | 2/1978 | Fed. Rep. of Germany ...... 514/227 |

OTHER PUBLICATIONS

Jones, R. G. J. Am. Chem. Soc. 71, 644, 645 (1949).
Marsh, R. W., "Systemic Fungicides," 2nd edition, 1977 pp. 71-73.
Buchel, K. H., "Chemistry of Pesticides," Wiley-Interscience, 1982, p. 306.

*Primary Examiner*—Allen J. Robinson

[57] ABSTRACT

Fungicidal compositions comprise at least one morpholine-type fungicide and at least one imidazole derivative of general formula (I):

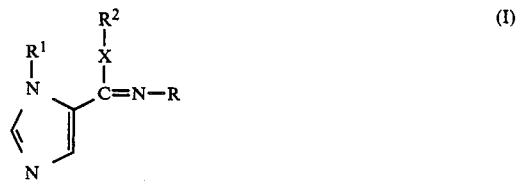

or a salt thereof; where R represents an optionally substituted phenyl group, $R^1$ represents an optionally substituted alkyl, cycloalkyl, alkenyl, aryl or aralkyl group, $R^2$ represents an optionally substituted alkyl, cycloalkyl, cycloalkylalkyl, alkenyl, alkynyl, aryl or aralkyl group, and X represents an oxygen or sulphur atom or a group —$NR^3$—, where $R^3$ represents a hydrogen atom or an optionally substituted alkyl group or $R^2$ and $R^3$ together with the interjacent nitrogen atom represent a 5- or 6- member saturated or unsaturated heterocyclic ring optionally containing one or two further heteroatoms. The compositions are particularly useful in combating wheat leaf spot and powdery mildews.

8 Claims, No Drawings

FUNGICIDAL COMPOSITIONS

This invention relates to fungicidal compositions and is particularly concerned with the preparation and use of compositions comprising morpholine-type fungicides in combination with certain imidazole derivatives.

The use of morpholine-type fungicides in combating barley powdery mildew (*E. graminis*) is well known (see "Systemic Fungicides", Second Edition, 1977 edited by R. W. Marsh, Longman and "Chemistry of Pesticides," 1982, edited by K. H. Buchel, Wiley-Interscience) Examples of such morpholine-type fungicides include 2,6-dimethyl-4-tridecylmorpholine ("Tridemorph"), a systemic and eradicant fungicide effective against cereal mildews, 2,6-dimethyl-4-cyclododecylmorpholine ("Dodemorph"), a systemic fungicide effective against powdery mildews on roses and 2,6-dimethyl-4-(2-methyl-3-(4-tert-1-butylphenyl))-propylmorpholine ("Fenpropimorph"), effective against powdery mildews and rusts.

However such morpholine derivatives have been found to be narrow spectrum fungicides. In particular they have been found not to be effective against such diseases as wheat leaf spot.

Recently, a new class of imidazole derivatives has been developed which have been found to be useful as broad spectrum fungicides, including use in combating both powdery mildews and wheat leaf spot.

Surprisingly, it has been found that such imidazole compounds can be used in combination with morpholine-type fungicides to give enhanced activity against diseases such as wheat leaf spot.

According to the present invention there is provided a composition comprising at least one morpholine-type fungicide and at least one imidazole derivative of general formula (I):

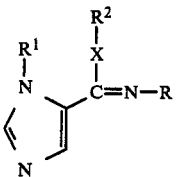
(I)

or a salt thereof; where R represents an optionally substituted phenyl group, $R^1$ represents an optionally substituted alkyl, cycloalkyl, alkenyl, aryl or aralkyl group, $R^2$ represents an optionally substituted alkyl, cycloalkyl, cycloalkylalkyl, alkenyl, alkynyl, aryl or aralkyl group, and X represents an oxygen or sulphur atom or a group $-NR^3-$, where $R^3$ represents a hydrogen atom or an optionally substituted alkyl group or $R^2$ and $R^3$ together with the interjacent nitrogen atom represent a 5- or 6-membered saturated or unsaturated heterocyclic ring optionally containing one or two further heteroatoms.

The alkyl, alkenyl and alkynyl groups may be linear or branched and preferably have from 1 to 8 carbon atoms.

Optional substituents include for example halogen atoms and alkyl, alkoxy, haloalkyl, haloalkoxy, hydroxy, cyano, nitro, amino, carboxy, alkoxycarbonyl, phenyl, phenoxy, phenylthio, alkylthio and alkylsulphonyl groups, any alkyl moiety present preferably having up to 4 carbon atoms.

R is preferably a phenyl group optionally substituted by a phenoxy group, a trifluoromethyl group, a methoxy group, a nitro group and/or by 1 to 5 halogen atoms. Advantageously R is a phenyl group substituted by 1 to 3 halogen, preferably chlorine, bromine or fluorine, atoms or by a trifluoromethyl group and one or two halogen, preferably chlorine, bromine or fluorine, atoms $R^1$ is preferably a $C_{1-12}$ alkyl, conveniently a $C_{1-7}$ alkyl, group, a $C_{3-8}$ cycloalkyl group, a $C_{2-6}$ alkenyl group, a phenyl group or a benzyl group.

$R^2$ is preferably a $C_{1-6}$ alkyl or haloalkyl group, a $C_{3-8}$ cycloalkyl group, a ($C_{3-8}$ cycloalkyl)methyl group, a $C_{3-6}$ alkenyl group, a phenyl group or a benzyl group, while X is preferably $-O-$, $-S-$ or $-NR^3-$, and $R^3$ is a hydrogen atom or a $C_{1-6}$ alkyl group, or $R^2$ and $R^3$ together with the interjacent nitrogen atom represent a triazole or pyrrolidine ring.

Alternatively $R^2$ is a group of the formula $(CR^4R^5)_m-C\equiv C-R^6$ where m is 1 to 4 and $R^4$, $R^5$ and $R^6$ are each independently a hydrogen atom or an optionally substituted alkyl or alkenyl group, provided that, where m is 1, $R^4$ is a hydrogen atom.

Preferably, each of $R^4$, $R^5$ and $R^6$ is a hydrogen atom or an alkyl group having up to 8 carbon atoms. Preferred compounds are those in which m is 1, $R^4$ is hydrogen and each of $R^5$ and $R^6$ is hydrogen or methyl. When $R^2$ is an alkynyl group X is preferably an oxygen atom or the group $-NR^3-$, $R^3$ preferably being hydrogen.

A particularly preferred sub-group of compounds of formula I is that wherein R is a 2,4-dichlorophenyl, 2,4-difluorophenyl or 4-chloro-2-trifluoromethylphenyl group, $R^1$ is a $C_{1-7}$ alkyl group, X is $-O-$, $-S-$ or $-NCH_3$ and $R^2$ is a $C_{1-6}$ alkyl, e.g. ethyl or isopropyl, or $C_{3-4}$ alkenyl, e.g. allyl or 3-but-1-enyl, group. Particularly preferred compounds of formula (I) are those in which $R^1$ is a methyl group, R is a 2,4-dichlorophenyl group, X is an oxygen atom and $R^2$ is a secondary butyl or 3-pentyl group.

An alternative subgroup of compounds of formula I is that wherein R is a 2,4-dichlorophenyl, 2,5-dichlorophenyl, 4-chloro-2-trifluoromethylphenyl, 4-methoxyphenyl or 4-chloro-2-nitrophenyl group. $R^1$ is an alkyl or alkenyl group having up to 8 carbon atoms or a benzyl group, X is an oxygen atom or the group $-NH-$, $R^2$ is of the formula $-CHR^5-C\equiv C-R^6$ and $R^5$ and $R^6$ are each independently hydrogen or methyl.

The compounds of formula (I) may be used in the composition of the invention in the form of imidazole salts such as salts with suitable inorganic moieties such as reactive metals of mineral acids, e.g. HCl.

Examples of the preparation of compounds of formula I are given in our copending European Applications Nos. 0191514 and 87201335.4.

The compounds of formula (I) may be prepared by reacting a compound of formula (II)

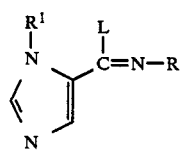
(II)

wherein R and $R^1$ are as defined above and L is a leaving group, with a compound of formula (III)

H—X—R²     (III)

where R² and X are as defined above, in the presence of a base.

The leaving group L may conveniently be a chlorine or bromine atom.

In some cases, e.g. when X is —O—, the compound of formula (III) may advantageously be treated with the base prior to admixture with the compound of formula (II). Thus for example, when the compound of formula (III) is an alkanol, the mixture of the compound of formula (III) with base may be achieved by dissolving sodium metal in the alkanol or by reaction of the alkanol with sodium hydride. In cases where X is —NR³—, the base may be an excess of compound of formula (III) or it may be a base such as pyridine. In cases where X is —S—, the base may conveniently be a base such as pyridine.

The above process may be effected in the absence of an additional inert solvent, e.g. when the compound of formula (III) is in excess and the excess acts as a solvent, or in cases when e.g. pyridine is used as the base and itself acts as a solvent. Alternatively an additional, inert solvent may be present. Suitable solvents include dimethoxyethane, dimethylsulphoxide, N,N-dimethylformamide and tetrahydrofuran. Dimethoxyethane and dimethylsulphoxide have been found to be very suitable.

Compounds of formula (II), wherein L is Cl or Br, may conveniently be prepared by reacting a compound of formula

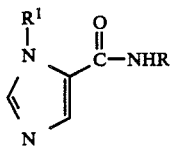
    (IV)

where R and R¹ are as defined above, with a halogenating agent. Suitable halogenating agents include thionyl chloride, phosphorous pentachloride, phosphorous trichloride and phosphorous tribromide. Such reaction may, if desired, be effected in the presence of an inert solvent such as toluene, benzene, diethyl ether or tetrahydrofuran.

Compounds of formula (IV) are either known compounds or can be prepared by processes analogous to known processes, e.g. to processes described in R. G. Jones, J.Am.Chem.Soc 71 (1949), 644 or in DE-A-3 217 094.

The morpholine-type fungicide is preferably of formula (V):

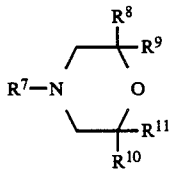
    (V)

where R⁷ is an optionally substituted alkyl, cycloalkyl or aralkyl group and each of R⁸, R⁹, R¹⁰ and R¹¹ is selected from hydrogen atoms and optionally substituted alkyl groups. Optional substituents include those given above for compounds of formula (I).

The compounds of formula (V) may be employed in the composition of the invention in any suitable form, for example as salts, such as salts with inorganic or organic acids, e.g. acetic acid, N-oxides or metal complexes.

Preferred compounds of formula (V) are those in which R⁸ and R¹⁰ each represent a hydrogen atom and R⁹ and R¹¹ each represent a methyl group. Preferably R⁷ is a straight chain alkyl group having 9 to 18 carbon atoms; e.g. C₁₃H₂₇—, a cycloalkyl group having 6 to 13 carbon atoms, e.g. cyclododecyl, or an aralkyl group having 9 to 18 carbon atoms, e.g. 2-methyl-3-(4-tert-butylphenyl)-propyl. Particularly preferred compounds are 2,6-dimethyl-4-tridecylmorpholine and 2,6-dimethyl-4-(2-methyl-3-(4-tert-butylphenyl)) propylmorpholine.

The morpholine-type fungicide and imidazole derivative may be present in the composition of the invention in relative amounts which vary widely dependent on the intended use. Furthermore, mixtures of morpholine-type fungicides and/or mixtures of imidazole derivatives can be employed. However the ratio of morpholine-type fungicide to imidazole derivative is usually from 0.1:1 to 5:1 based on parts by weight of active ingredients, preferably 0.5:1 to 3:1 and most preferably 0.5 to 1.5:1.

A preferred composition in accordance with the invention comprises 2,6-dimethyl-4-tridecylmorpholine and an imidazole derivative of formula (I) in which R is a 2,4-dichlorophenyl group, X is an oxygen atom and R² is a secondary butyl group, the weight ratio of morpholine-type compound to imidazole derivative preferably being from 0.5:1 to 1.5:1. A further Preferred composition comprises 2,6-dimethyl-4-trideylmorpholine and an imidazole derivative of formula (I) in which R is a 2,4-dichlorophenyl group, X is an oxygen atom and R² is a 3-pentyl group, the weight ratio of morpholine-type compound to imidazole derivative preferably being from 0.5:1 to 3:1.

Further preferred compositions comprise 2,6-dimethyl-4-(2-methyl-3-(4-tert-butylphenyl))-propylmorpholine and an imidazole derivative of formula (I) in which R is a 2,4-dichlorophenyl group, X is an oxygen atom and R² is a secondary butyl or 3-phenyl group.

The composition of the invention suitably comprises a carrier, the active ingredients being present in a total amount of 0.5 to 95% by weight.

A carrier in the composition according to the invention is any material with which the active ingredients are formulated to facilitate application to the locus to be treated, which may for example be a plant, seed or soil, or to facilitate storage, transport or handling. A carrier may be a solid or a liquid. including a material which is normally gaseous but which has been compressed to form a liquid, and any of the carriers normally used in formulating fungicidal compositions may be used. Liquid carriers are however preferred.

Suitable solid carriers include natural silicas such as diatomaceous earths; magnesium silicates, for example talcs; magnesium aluminium silicates, for example attapulgites and vermiculites; aluminium silicates, for example kaolinites, montmorillonites and micas; calcium carbonates; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloiide, perchloroethylene and trichloroethane. Mixtures of different liquids are often suitable.

Fungicidal compositions are often formulated and transported in a concentrated form which is subsequently diluted by the user before application. The presence of small amounts of a carrier component which is a surface-active agent facilitates this process of dilution. Thus, preferably at least one carrier component in the composition according to the invention is a surface-active agent. For example, a composition may contain at least two carrier components, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecyl benzene sulphonate; and polymers of ethylene oxide and copolymers of ethylene oxide and propylene oxide.

The composition of the invention may for example be formulated as wettable powders, dusts, granules, solutions, emulsifiable concentrates, emulsions, suspension concentrates and aerosols. Wettable powders usually contain 25, 50 or 75% by weight of active ingredient and usually contain, in addition to solid inert carrier, 3.10% by weight of a dispersing agent and, where necessary, 0–10% by weight of stabiliser and/or other additives such as penetrants or stickers. Dusts are usually formulated as a dust concentrate having a similar composition to that of a wettable powder but without a dispersant, and may be diluted in the field with further solid carrier to give a composition usually containing 0.5–10% by weight of active ingredient. Granules are usually prepared to have a size between 10 and 100 BS mesh (1.676–0.152 mm), and may be manufactured by agglomeration or impregnation techniques. Generally, granules will contain 0.5–25% by weight of active ingredients 0–10% by weight of additives such as stabilisers, slow release modifiers and binding agents. Emulsifiable concentrates usually contain, in addition to a solvent and, when necessary, cosolvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% by weight of active ingredients, 0.5–15% by weight of dispersing agents, 0.1–10% by weight of suspending agents such as protective colloids and thixotropic agents, 0–10% by weight of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the present invention. The said emulsions may be of the water-in-oil or of the oil in-water type, and may have a thick "mayonnaise"-like consistency.

Of particular interest in enhancing the duration of the protectant activity of the composition of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The compositions may also contain other ingredients, for example other compounds possessing pesticidal, especially insecticidal, acaricidal, herbicidal or fungicidal, properties.

The invention includes the use of the composition of the invention in a method for combating fungus at a locus, which comprises treating the locus, which may, for example, be plants subject to or subjected to fungal attack, seeds of such plants or the medium in which such plants are growing or are to be grown, with such a composition.

The present invention is of wide applicability in the protection of crop plants against fungal attack. Typical crops which may be protected include vines, grain crops such as wheat and barley, rice, beans and apples, peanuts and bananas. The duration of protection is normally dependent on the individual compound selected, and also a variety of external factors, such as climate, whose impact is normally mitigated by the use of a suitable formulation. Application rates may typically be in the range 0.1 to 10 kg active ingredient per hectare (kg/ha), preferably 0.1 to 1 kg/ha.

However, the compositions of the invention have been found to be particularly effective in combating wheat leaf spot in that the presence of the morpholine-type fungicide, itself substantially inactive against wheat leaf spot, gives a composition exhibiting synergism with increased activity against wheaf leaf spot over and above that of the imidazole derivative alone.

The invention will now be further described by way of example.

EXAMPLE 1

Preparation of 1-methylpropyl-N-(2,4-dichlorophenyl)-1-methylimidazole-5-carboximidate [(I)]

(R=2,4-dichlorophenyl; $R^1$=$CH_3$; X=0; $R^2$=sec.butyl)

N-(2,4-Dichlorophenyl-1-methyl-5-carboximidate (2.0 g) was refluxed in thionyl chloride (50 ml) for 2 hours. The excess thionyl chloride was evaporated off under reduced pressure and the solid residue was suspended in dimethoxyethane (50 ml). To this suspension was added a solution of sodium (0.4 g) in sec.butanol (40 ml). The reaction mixture was stirred and refluxed for 12 hours. On cooling, the solvent was evaporated off under reduced pressure and the residue diluted with water and extracted with chloroform. The organic extracts were dried (using $MgSO_4$) and the solvent evaporated off to leave a brown oil. Column chromatography on silica using 2% methanol chloroform as eluant afforded 1-methylpropyl-N-(2,4-dichlorophenyl)-1-methylimidazole-5-carboximidate (1.2 g; 50%) as a pale yellow oil.

Found: C, 55.4; H, 4.9; N, 12.9. $C_{15}H_{17}Cl_2N_3O$ requires: C, 53.3; H, 5.0; N, 12.5.

EXAMPLE 2

Preparation of Fungicidal Compositions

The compound prepared in accordance with Example 1 was combined with 2,6-dimethyl-4-tridecylmorpholine for use in fungicidal tests as described below. Two combination methods were used for making compositions in accordance with the invention, i.e:

Method A

The imidazole derivative of Example 1 and 2,6-dimethyl-4-tridecylmorpholine ("Tridemorph" - BASF) were mixed together in varying weight ratios using castor oil ethoxylate as emulsifier and isobutanol to give a formulated concentrate before the addition of water to give a sprayable composition.

Method B

The compound of Example 1 and "Tridemorph" were not pre-mixed but were separately included in a tank-mix with the carrier to give a sprayable composition.

The ratios of imidazole derivative ("azole") and "Tridemorph", based on weights of active ingredient, and the combination method used are given in Tables 1 to 4 below.

EXAMPLE 3

Activity against wheat leafspot (*Leptosphaeria nodorum;* Ln)

This is a direct antisporulant test, using a foliar spray. Leaves of wheat plants (cv Mardler), at the single leaf stage, are inoculated by spraying with an aqueous suspension containing $8 \times 10^5$ spores/ml. The inoculated plants are kept for 24 hours in a high humidity compartment prior to treatment. The plants are sprayed at varying dosages of active material per hectare as given in Tables 1 and 2 using a track sprayer which delivers 620 l/ha. After drying. the plants are kept under normal glasshouse conditions, with assessment 7 days or 10 days after treatment. Assessment is based on the percentage of leaf area covered by sporulation compared with that on leaves of control plants on a visual assessment scale of 0 to 9 in which:

0=0-9% disease control
1=10-19% disease control
up to 9=90-100% disease control

Three runs were carried out for each set of test conditions and the mean values are given in Table 1. Table 1 gives assessment taken 10 days after treatment and 7 days after treatment. Tests 21 to 25 in each case used the imidazole derivatives of Example 1 alone and Tests 26 to 30 used "Tridemorph" alone as the commercially available formulation "Calixin" (BASF). Test 31 was a control with untreated plants, the mean value being based on six runs.

TABLE 1

| Test No. | Combination Method | Ln-Assessment Ratio Azole: Tridemorph | Dose Azole (g/ha) | Mean Assessment (10 days) | Mean Assessment (7 days) |
|---|---|---|---|---|---|
| 1 | B | 1:0.5 | 1 | 3.87 | 3.23 |
| 2 | B | 1:0.5 | 3 | 3.53 | 3.00 |
| 3 | B | 1:0.5 | 10 | 2.33 | 2.90 |
| 4 | B | 1:0.5 | 30 | 1.43 | 2.37 |
| 5 | B | 1:0.5 | 100 | 1.43 | 2.13 |
| 6 | B | 1:1 | 1 | 5.23 | 3.23 |
| 7 | B | 1:1 | 3 | 4.43 | 3.77 |
| 8 | B | 1:1 | 10 | 2.67 | 2.77 |
| 9 | B | 1:1 | 30 | 1.57 | 2.77 |
| 10 | B | 1:1 | 100 | 1.10 | 2.03 |
| 11 | A | 1:0.5 | 1 | 3.20 | 3.10 |
| 12 | A | 1:0.5 | 3 | 2.10 | 2.70 |
| 13 | A | 1:0.5 | 10 | 2.47 | 2.90 |
| 14 | A | 1:0.5 | 30 | 1.90 | 2.00 |
| 15 | A | 1:0.5 | 100 | 1.00 | 1.10 |
| 16 | A | 1:1 | 1 | 2.43 | 2.77 |
| 17 | A | 1:1 | 3 | 2.30 | 2.77 |
| 18 | A | 1:1 | 10 | 1.67 | 2.00 |
| 19 | A | 1:1 | 30 | 1.23 | 1.67 |
| 20 | A | 1:1 | 100 | 1.20 | 0.67 |
| 21 | AZOLE ALONE | — | 1 | 5.23 | 5.03 |
| 22 | " | — | 3 | 4.27 | 4.70 |
| 23 | " | — | 10 | 3.73 | 3.80 |
| 24 | " | — | 30 | 3.83 | 3.90 |
| 25 | " | — | 100 | 3.20 | 3.50 |

TABLE 1-continued

| Test No. | Combination Method | Ln-Assessment Ratio Azole: Tridemorph | Dose Azole (g/ha) | Mean Assessment (10 days) | Mean Assessment (7 days) |
|---|---|---|---|---|---|
| 26 | TRIDEMORPH ALONE | — | 1* | 5.77 | 4.47 |
| 27 | TRIDEMORPH ALONE | — | 3* | 5.63 | 4.23 |
| 28 | TRIDEMORPH ALONE | — | 10* | 5.77 | 3.90 |
| 29 | TRIDEMORPH ALONE | — | 30* | 5.23 | 4.00 |
| 30 | TRIDEMORPH ALONE | — | 100* | 4.53 | 3.97 |
| 31 | CONTROL | — | — | 7.00 | 4.97 |

*Dose given as g/ha "Tridemorph"

It will be seen from Table 1 that there are significant differences between the results (Tests 1 to 20) obtained using a combination of imidazole derivative and "Tridemorph" showing the presence of a synergistic effect.

EXAMPLE 4

Activity against barley powdery mildew (*Erysiphe graminis* f.s.p *hordei*; Eg)

This is a direct antisporulant test, using a foliar spray. Leaves of barley seedlings, cultivar Golden Promise, are inoculated by dusting with mildew conidia one day prior to treatment with the test compound. The inoculated plants are kept overnight at glasshouse ambient temperature and humidity prior to treatment. The plants are sprayed at varying dosages of active material per hectare using a track sprayer which delivers 620 l/ha. After drying, plants are returned to a compartment at ambient temperature and humidity, with assessment 6 or 8 days after treatment. Assessment is based on the percentage of leaf area covered by sporulation compared with that on leaves of control plants.

Three runs were carried out for each set of test conditions and the mean values (% cover) and overall effectiveness (% effect) are given in Table 2 and 3. Table 2 gives assessments taken 8 days after treatment and Table 3 gives assessments 6 days after treatment. Tests 21 to 25 used the imidazole derivative of Example 1 alone and Tests 26 to 30 used "Tridemorph" alone as the commercially available formulation "Calixin" (BASF). Test 31 was a control with untreated plants, the mean values being based on six runs.

TABLE 2

| Test No. | Combination Method | Eg-Assessment 8 days after treatment Ratio Azole: Tridemorph | Dose Azole (g/ha) | Mean Assessment (% Cover) | % Effect |
|---|---|---|---|---|---|
| 1 | B | 1:0.5 | 1 | 6.60 | 79.3 |
| 2 | B | 1:0.5 | 3 | 3.93 | 87.6 |
| 3 | B | 1:0.5 | 10 | 0.20 | 99.4 |
| 4 | B | 1:0.5 | 30 | 0.00 | 100.0 |
| 5 | B | 1:0.5 | 100 | 0.00 | 100.0 |
| 6 | B | 1:1 | 1 | 5.87 | 81.6 |
| 7 | B | 1:1 | 3 | 2.87 | 91.0 |
| 8 | B | 1:1 | 10 | 2.20 | 93.1 |
| 9 | B | 1:1 | 30 | 0.00 | 100.0 |
| 10 | B | 1:1 | 100 | 0.00 | 100.0 |
| 11 | A | 1:0.5 | 1 | 6.00 | 81.2 |
| 12 | A | 1:0.5 | 3 | 1.27 | 96.0 |
| 13 | A | 1:0.5 | 10 | 0.60 | 98.1 |
| 14 | A | 1:0.5 | 30 | 0.00 | 100.0 |
| 15 | A | 1:0.5 | 100 | 0.00 | 100.0 |
| 16 | A | 1:1 | 1 | 5.47 | 82.8 |
| 17 | A | 1:1 | 3 | 0.87 | 97.3 |
| 18 | A | 1:1 | 10 | 0.13 | 99.6 |
| 19 | A | 1:1 | 30 | 0.00 | 100.0 |
| 20 | A | 1:1 | 100 | 0.00 | 100.0 |
| 21 | AZOLE ALONE | — | 1 | 15.23 | 52.1 |
| 22 | " | — | 3 | 9.10 | 71.4 |
| 23 | " | — | 10 | 6.83 | 78.5 |
| 24 | " | — | 30 | 2.83 | 91.1 |
| 25 | " | — | 100 | 0.00 | 100.0 |
| 26 | TRIDEMORPH ALONE | — | 1* | 20.80 | 34.7 |
| 27 | TRIDEMORPH ALONE | — | 3* | 8.20 | 74.2 |
| 28 | TRIDEMORPH ALONE | — | 10* | 3.20 | 89.9 |
| 29 | TRIDEMORPH ALONE | — | 30* | 0.20 | 99.9 |
| 30 | TRIDEMORPH ALONE | — | 100* | 0.00 | 100.0 |
| 31 | CONTROL | — | — | 31.83 | 0.0 |

*Dose given as g/ha "Tridemorph"

TABLE 3

| Test No. | Combination Method | Eg-Assessment 6 days after treatment Ratio Azole: Tridemorph | Dose Azole (g/ha) | Mean Assessment (% Cover) | % Effect |
|---|---|---|---|---|---|
| 1 | B | 1:0.5 | 1 | 2.00 | 92.4 |
| 2 | B | 1:0.5 | 3 | 1.33 | 95.0 |
| 3 | B | 1:0.5 | 10 | 0.07 | 99.7 |
| 4 | B | 1:0.5 | 30 | 0.07 | 99.7 |
| 5 | B | 1:0.5 | 100 | 0.00 | 100.0 |
| 6 | B | 1:1 | 1 | 1.47 | 94.5 |
| 7 | B | 1:1 | 3 | 0.00 | 100.0 |
| 8 | B | 1:1 | 10 | 0.00 | 100.0 |
| 9 | B | 1:1 | 30 | 0.00 | 100.0 |
| 10 | B | 1:1 | 100 | 0.00 | 100.0 |
| 11 | A | 1:0.5 | 1 | 0.27 | 99.0 |
| 12 | A | 1:0.5 | 3 | 0.00 | 100.0 |
| 13 | A | 1:0.5 | 10 | 0.00 | 100.0 |
| 14 | A | 1:0.5 | 30 | 0.00 | 100.0 |
| 15 | A | 1:0.5 | 100 | 0.00 | 100.0 |
| 16 | A | 1:1 | 1 | 1.60 | 94.0 |
| 17 | A | 1:1 | 3 | 0.00 | 100.0 |
| 18 | A | 1:1 | 10 | 0.00 | 100.0 |
| 19 | A | 1:1 | 30 | 0.00 | 100.0 |
| 20 | A | 1:1 | 100 | 0.00 | 100.0 |
| 21 | AZOLE ALONE | — | 1 | 4.40 | 83.4 |
| 22 | " | — | 3 | 4.23 | 84.0 |
| 23 | " | — | 10 | 2.07 | 92.2 |
| 24 | " | — | 30 | 0.03 | 99.9 |
| 25 | " | — | 100 | 0.00 | 100.0 |
| 26 | TRIDEMORPH | — | 1* | 13.60 | 48.6 |

TABLE 3-continued

Eg-Assessment 6 days after treatment

| Test No. | Combination Method | Ratio Azole: Tridemorph | Dose Azole (g/ha) | Mean Assessment (% Cover) | % Effect |
|---|---|---|---|---|---|
| 27 | TRIDEMORPH ALONE | — | 3* | 1.27 | 95.2 |
| 28 | TRIDEMORPH ALONE | — | 10* | 0.40 | 98.5 |
| 29 | TRIDEMORPH ALONE | — | 30* | 0.00 | 100.0 |
| 30 | TRIDEMORPH ALONE | — | 100* | 0.00 | 100.0 |
| 31 | CONTROL | — | — | 26.47 | 0.0 |

*Dose given as g/ha "Tridemorph"

EXAMPLE 5

Preparation of 1-ethylpropyl-N-(2,4-dichlorophenyl)-1-methyl imidazole-5-carboximidate N-(2,4-dichlorophenyl)-1-methylimidazole-5-carboxamide (2.0 g) was refluxed in thionyl chloride (50 ml) for 2 hours. Excess thionyl chloride was evaporated off and the residue suspended in dimethoxyethane (25 ml). A solution of sodium (0.4 g) in pentan-3-ol (35 ml) was added to the solution and the reaction mixture refluxed for 18 hours. After cooling, the solvent was evaporated off under reduced pressure and the residue taken up in chloroform, washed with water and dried with magnesium sulphate. The chloroform was evaporated off under reduced pressure to give an oil. which was chromatographically purified to yield the desired product as a pale yellow oil.

Analysis Found: C 56.5; H 5.7; N 12.3. $C_{16}H_{19}Cl_2N_3O$ Requires: C 56.5; H 5.6; N 12.3.

EXAMPLE 6

Fungicidal Activity

Mixtures of the compound of Example 5 with 2,6-dimethyl-4-tridecylmorpholine ("Tridemorph") and 2,6-dimethyl-4-(2-methyl-3-(4-tert-butylphenyl))-propylmorpholine ("Fenpropimorph") were tested for activity against wheat powdery mildew (*Erysiphe graminis;* Eg) using a similar method to that described in Example 4 but using wheat seedlings instead of barley seedlings.

The results are set out in Table 4 below.

TABLE 4

Eg: Assessment 9 days after treatment

| Composition | Test No. | Ratio Azole: Morpholine | Dose Azole (g/ha) | % cover | % effect |
|---|---|---|---|---|---|
| Compound of Ex. 5 + Tridemorph | 1 | 1:0.5 | 10 | 3.4 | 94.9 |
|  | 2 | 1:3 | 100 | 0.0 | 100.0 |
|  | 3 | 1:3 | 200 | 0.0 | 100.0 |
| Compound of Ex. 5 + Fenpropimorph | 4 | 1:1 | 10 | 4.7 | 92.9 |
|  | 5 | 1:1 | 100 | 0.0 | 100.0 |
|  | 6 | 1:1 | 200 | 0.0 | 100.0 |
| Compound of Ex. 5 | 7 | — | 10 | 2.8 | 95.8 |
|  | 8 | — | 100 | 1.0 | 98.5 |
|  | 9 | — | 200 | 0.0 | 100.0 |
| Untreated Control | 10 | — | — | 66.5 | 0.0 |

We claim:

1. A composition comprising a morpholine-type fungicide selected from the group consisting of 2,6-dimethyl-4-tridecylmorpholine and 2,6-dimethyl-4-(2-methyl-3-(4-tert-butylphenyl))-propylmorpholine and a imidazole derivative of formula (I):

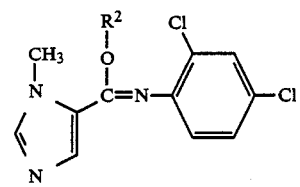

where $R^2$ represents an alkyl group having 4 or 5 carbon atoms, in which the ratio of morpholine-type fungicide to imidazole derivative is from 1:2 to 3:1 based on parts by weight of active ingredients.

2. A composition according to claim 1 in which $R^2$ is a 2-butyl or 3-pentyl group.

3. A composition according to claim 2 in which the morpholine-type fungicide is 2,6-dimethyl-4-tridecylmorpholine, the imidazole derivative is 1-methylpropyl-N-(2,4-dichlorophenyl)-1-methylimidazole-5-carboximidate and the ratio of morpholine-type fungicide to imidazole derivative is from 1:2 to 1:1.

4. A composition according to claim 2 in which the morpholine-type fungicide is 2,6-dimethyl-4-tridecylmorpholine, the imidazole derivative is 1-ethylpropyl-N-(2,4-dichlorophenyl)-1-methylimidazole-5-carboximidate and the ratio of morpholine-type fungicide to imidazole derivative is from 1:2 to 3:1.

5. A composition according to claim 2 in which the morpholine-type fungicide is 2,6-dimethyl-4-(2-methyl-3-(4-tertbutylphenyl)-propylmorpholine, the imidazole derivative is 1-ethylpropyl-N-(2,4-dichlorophenyl)-1-methylimadizole-5-carboximidate and the ratio of morpholine-type fungicide to imidazole derivative is 1:1.

6. A method of combating cereal fungal disease which comprises treating cereal plants subject or subjected to fungal attack, seeds of such plants or the medium in which the plants are growing or are to be grown with a composition according to claim 1 at a dosage of from 1 to 200 g/ha of the imidazole derivative.

7. A method according to claim 6 in which the cereal plants are wheat or barley plants.

8. A method according to claim 7 in which the cereal fungal disease is wheat leafspot or barley powdery mildew.

* * * * *